United States Patent
Li

(10) Patent No.: US 10,493,049 B2
(45) Date of Patent: Dec. 3, 2019

(54) APPLICATOR-BASED TRANSDERMAL DRUG DELIVERY SYSTEM FOR ADMINISTRATION OF DRUGS IN COMBINATION WITH TOPICAL FORMULATIONS

(71) Applicant: Niracle LLC, Newton, PA (US)

(72) Inventor: Weiyong Li, Newton, PA (US)

(73) Assignee: NIRACLE LLC, Newton, PA (US)

( * ) Notice: Subject to any disclaimer, the term of this patent is extended or adjusted under 35 U.S.C. 154(b) by 0 days.

(21) Appl. No.: 15/426,468

(22) Filed: Feb. 7, 2017

(65) Prior Publication Data

US 2017/0224642 A1  Aug. 10, 2017

Related U.S. Application Data

(60) Provisional application No. 62/293,652, filed on Feb. 10, 2016.

(51) Int. Cl.
*A61K 31/192* (2006.01)
*A61K 9/70* (2006.01)
*A61M 37/00* (2006.01)

(52) U.S. Cl.
CPC ........... *A61K 31/192* (2013.01); *A61K 9/703* (2013.01); *A61K 9/7084* (2013.01); *A61M 37/00* (2013.01)

(58) Field of Classification Search
CPC ...... A61K 31/192; A61K 9/703; A61K 9/084; A61K 37/00
See application file for complete search history.

(56) References Cited

U.S. PATENT DOCUMENTS

| | | | |
|---|---|---|---|
| 3,964,482 A * | 6/1976 | Gerstel | A61K 9/0021 604/890.1 |
| 4,626,539 A | 12/1986 | Aungst et al. | |
| 4,956,171 A | 9/1990 | Chang et al. | |
| 5,152,997 A | 10/1992 | Ebert et al. | |
| 5,736,154 A | 4/1998 | Fuisz et al. | |
| 5,817,332 A | 10/1998 | Urtti et al. | |
| 5,866,143 A | 2/1999 | El Khoury et al. | |
| 5,891,462 A | 4/1999 | Carrara et al. | |
| 5,902,602 A | 5/1999 | Chen et al. | |
| 5,948,433 A | 9/1999 | Burton et al. | |
| 6,011,022 A | 1/2000 | El Khoury et al. | |
| 6,335,030 B1 | 1/2002 | Hoeck et al. | |
| 6,756,052 B1 | 6/2004 | Koch et al. | |
| 7,537,590 B2 | 5/2009 | Santni, Jr. et al. | |
| 8,696,637 B2 | 4/2014 | Ross | |
| 8,834,447 B2 | 9/2014 | Chen et al. | |
| 9,161,915 B2 | 10/2015 | Fossel | |

(Continued)

*Primary Examiner* — Lauren P Farrar

(57) ABSTRACT

An applicator-based transdermal drug delivery system (ABTDS) for administration of drugs to a patient to treat ailments in combination with a wide range of topical formulation classes including but not limited to creams, foams, gels, lotions, and ointments is described herein. The transdermal drug delivery system utilizes an applicator that can be in various disk-like shapes and sizes, and that contain the topical formulation in a fixed area, and is applied over the skin of the patient to ensure accurate drug delivery and protect the drug from being rubbed away. Additional features of the applicator include numerous blunt spikes present on its surface that are designed to enhance rate of drug delivery.

14 Claims, 2 Drawing Sheets

(56) References Cited

U.S. PATENT DOCUMENTS

| | | | |
|---|---|---|---|
| 2003/0065294 A1* | 4/2003 | Pickup | A01K 11/005 604/304 |
| 2006/0078604 A1 | 4/2006 | Kanios et al. | |
| 2010/0256174 A1* | 10/2010 | Yamaguchi | A61K 9/0014 514/282 |
| 2011/0224515 A1* | 9/2011 | Mir | A61B 5/14532 600/317 |
| 2012/0238970 A1* | 9/2012 | Royds | A61K 9/7084 604/307 |
| 2013/0046244 A1* | 2/2013 | Kinuta | A61K 8/676 604/180 |
| 2014/0243788 A1* | 8/2014 | Cantor | A61M 37/0015 604/506 |
| 2017/0095431 A1* | 4/2017 | Andrews | A61K 31/155 |

* cited by examiner

APPLICATOR-BASED TRANSDERMAL DRUG DELIVERY SYSTEM FOR ADMINISTRATION OF DRUGS IN COMBINATION WITH TOPICAL FORMULATIONS

The current application claims a priority to the U.S. Provisional Patent application Ser. No. 62/293,652 filed on Feb. 10, 2016.

FIELD OF THE INVENTION

The present invention is directed to the field of transdermal drug delivery system comprising an applicator which is mounted on a backing layer of a medical tape via an adhesive layer, and a topical formulation comprising a drug, wherein the applicator has a rim to define a sealed space, in which blunt spikes are present on the surface of the applicator, and wherein the topical formulation is filled in the space on the applicator between the spikes and the rim. The present invention also relates to a method of delivering a drug in a topical formulation to a patient by applying the transdermal drug delivery system to the skin of the patient.

BACKGROUND OF THE INVENTION

Transdermal drug delivery systems (TDDS) involve two major categories of products, namely transdermal (TD) patches and topical composition. TD patches have a well-defined contact area with the skin of a patient that will allow accurate administration of the drug from the drug-containing medium on the patch to the user through his/her skin. In addition, the drug delivery medium of the patch is protected when in use. Important TD patches that are commercially available include Duragesic® (fentanyl as active ingredient), Lidoderm (lidocaine as active ingredient) and Burtrans® (buprenorphine as active ingredient) for management of pain, Ortho Evra (ethinyl estradiol and norelgestromin as active ingredients) for contraceptive use, Daytrana® (methylphenidate as active ingredient) for attention deficient/hyperactivity disorder (ADHD), and Neupro® (rotigotine as active ingredient) for Parkinson's disease.

Most of the topical composition products are applied to a certain area of the skin and are intended to affect only the area to which they are applied. Commercially available examples include Emla® as a local anesthetic cream (lidocaine and prilocaine as active ingredients), Pennsaid solution (diclofenac as active ingredient) for pain caused by osteoarthritis, and Lotrisone cream (betamethasone and clotrimazol as active ingredients) for reducing itching, swelling, and redness of the skin. An exception is Elestrin gel (estradiol as active ingredient), which is an example of transdermal drug delivery using a topical formulation 7, for vasomotor symptoms (hot flash) due to menopause. But in general, topical composition products lack the mechanisms in controlling rate of drug delivery through a fixed area of the user's skin.

There are important advantages by taking the transdermal route for drug delivery when compared with the more conventional routes. One of them is the avoidance of hepatic first-pass metabolism. The other is simple discontinuation of medication if needed. An obvious disadvantage is that only very limited number of active pharmaceutical ingredients (API) are suitable for transdermal delivery.

Commercial manufacturing for products of TD patches requires sophisticated equipment and can be costly as compared with topical composition products. But TD patches offer much more accurate rate of drug delivery when compared with topical composition products. The delivery system in this invention combines the advantage of accurate drug delivery from a TD patch, and the advantages of topical composition product, which includes low cost in manufacturing and ease of use. A good example for application of the applicator/topical formulation combination is ibuprofen in a topical formulation 7 on the applicator 6 for reducing fever in infants and toddlers.

Ibuprofen is a nonsteroidal anti-inflammatory drug (NSAID) used widely for relieving pain, helping with fever, and reducing inflammation. One of the side effects for ibuprofen is gastrointestinal ulceration/bleeding, which can be avoided if it is administered trans-dermally. It is estimated that 20% of the pediatric emergency visit is related to fever (Alpern E R, Henretig F M. Fever. Fleisher G R, Ludwg S, Henretig F M, eds. Textbook of Pediatric Emergency Medicine. 5th ed. Philadelphia, Pa.: Lippincott Williams & Wilkins; 2006. 295-306). Therefore, a topical ibuprofen formulation that can be accurately delivered through skin, particularly targeted for infants and toddlers, can have important health benefits. Besides ibuprofen (Fossel, U.S. Pat. No. 9,161,915), other nonsteroidal anti-inflammatory drug (NSAID) such as ketoprofen and naproxen or other drugs such as opioids (Chang, U.S. Pat. No. 4,956,171; El Khoury U.S. Pat. No. 5,866,143; Kanios et al. US 20060078604), estrogen (Carrara, U.S. Pat. No. 5,891,462), analgesics (El Khoury, U.S. Pat. No. 6,011,022), antidepressant, and antihypertensives (Urtti et al., U.S. Pat. No. 5,817,332), antitussive (Hoeck et al., U.S. Pat. No. 6,335,030) are also suitable for transdermal delivery.

Transdermal delivery of drugs with various topical compositions has been cited (Aungst et al., U.S. Pat. No. 4,626,539; Ebert et al., U.S. Pat. No. 5,152,997; El Khoury, U.S. Pat. No. 5,866,143; Carrara, U.S. Pat. No. 5,891,462; El Khoury, U.S. Pat. No. 6,011,022). Various transdermal drug delivery systems including transdermal patch have also been reported (Chang et al., U.S. Pat. No. 4,956,171; Fuisz U.S. Pat. No. 5,736,154; Urtti et al., U.S. Pat. No. 5,817,332; Chen et al., U.S. Pat. No. 5,902,603; Burton et al., U.S. Pat. No. 5,948,433; Hoeck et al., U.S. Pat. No. 6,335,030; Koch et al., U.S. Pat. No. 6,756,052; Ross, U.S. Pat. No. 8,696,637; Santini, Jr., et al., U.S. Pat. No. 7,537,590; Chen et al., U.S. Pat. No. 8,834,447; Fossel, U.S. Pat. No. 9,161,915; Kanios et al., US 20060078604). All of which are incorporated by reference herein.

| Cited References (US Patent Documents) are listed as follows: | | |
| --- | --- | --- |
| 4,626,539 A | Aungst et al. | 514/282 |
| 4,956,171 A | Chang et al. | 424/449 |
| 5,152,997 A | Ebert et al. | 424/449 |
| 5,736,154 A | Fuisz et al. | 424/449 |
| 5,817,332 A | Urtti et al. | 424/449 |
| 5,866,143 A | El Khoury et al. | 424/401 |
| 5,891,462 A | Carrara et al. | 424/449 |
| 5,902,602 A | Chen et al. | 424/449 |
| 5,948,433 A | Burton et al. | 424/448 |
| 6,011,022 A | El Khoury et al. | 514/78 |
| 6,335,030 B1 | Hoeck et al. | 424/449 |
| 6,756,052 B1 | Koch et al. | 424/448 |
| 7,537,590 B2 | Santni, Jr. et al. | 604/890.1 |
| 8,696,637 B2 | Ross | 604/173 |
| 8,834,447 B2 | Chen et al. | 604/506 |
| 9,161,915 B2 | Fossel | 424/450 |
| 20060078604 A1 | Kanios et al. | 424/449 |

DETAIL DESCRIPTIONS OF THE INVENTION

Figure 1:
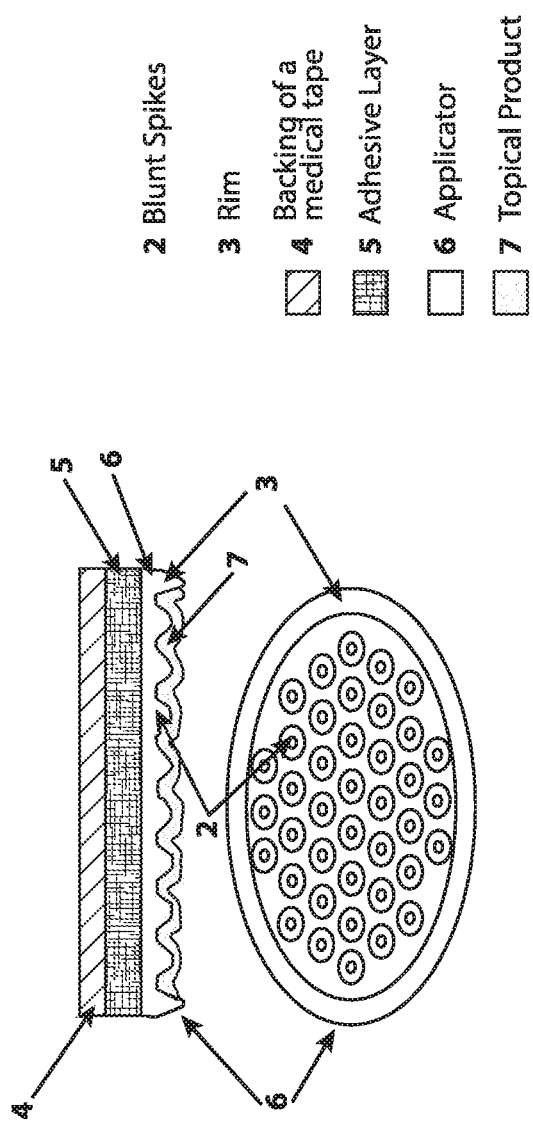
FIG. 1 is a schematic drawing of a transdermal drug delivery system showing the structure of an applicator which is mounted on a conventional medical tape via an adhesive layer in combination with a topical formulation.

All illustrations of the drawings are for the purpose of describing selected versions of the present invention and are not intended to limit the scope of the present invention.

In accordance with a first aspect of the present invention that provides a transdermal drug delivery system comprising an applicator 6 which is mounted on a backing layer of a medical tape 4 via an adhesive layer 5, and a topical formulation 7 comprising a suitable amount of a drug, wherein the suitable amount of drug penetrates the skin after applying the system to the skin of the patient, wherein the applicator 6 has a rim 3 to define a sealed space and has blunt spikes 2 present on its surface and in the space of rim 3; wherein the topical formulation 7 is filled in the space of the applicator 6 between the spikes and the rim 3; wherein the applicator 6 has different shapes and size, which can be optimized for delivering the suitable amount of the drug; and wherein the blunt spikes 2 serve the purpose of holding the topical formulation 7 and increasing the total surface area in contact with the skin when the system is applied to the patient, wherein the topical formulation 7 comprises (1) a suitable concentration of the drug (e.g., ibuprofen) in a pharmaceutically acceptable carrier for delivering a given dose of the active ingredient trans-dermally, (2) a component of a stabilizer and/or a skin penetration enhancer, and (3) various components with an optimized ratio to maintain chemical and physical stability of the drug delivery medium.

In accordance with a second aspect of the present invention, which provides a method for transdermal delivery of a drug (e.g. ibuprofen) comprising applying the transdermal drug delivery system to the skin of a patient, the transdermal drug delivery system comprising an applicator 6 which is mounted on a backing layer of a medical tape 4 via adhesive layer 5, and a topical formulation 7 comprising a suitable amount of a drug, wherein the suitable amount of drug penetrates the skin after applying the system to the skin of the patient, wherein the applicator 6 has a rim 3 to define a sealed space and has blunt spikes 2 present on its surface and in the space of rim 3; wherein the topical formulation 7 is filled in the space of the applicator 6 between the spikes and the rim 3; wherein the applicator 6 has different shapes and size, which can be optimized for delivering the suitable amount of the drug; and wherein the blunt spikes 2 serve the purpose of holding the topical formulation 7 and increasing the total surface area in contact with the skin when the system is applied to the patient, wherein the topical formulation 7 comprises (1) a suitable concentration of the drug (e.g., ibuprofen) in a pharmaceutically acceptable carrier for delivering a given dose of the active ingredient trans-dermally, (2) a component of a stabilizer and/or a skin penetration enhancer, and (3) various components with an optimized ratio to maintain chemical and physical stability of the drug delivery medium.

The "pharmaceutically acceptable carrier" as used herein refers to carrier materials suitable for transdermal drug administration, and includes any such material known in the art, e.g., any liquid, gel, solvent, liquid diluent, or solubilizer, which is nontoxic and which does not interact with other components of the composition. Examples of suitable pharmaceutically acceptable carriers for use herein include water, silicone, liquid sugars and other materials (Chen et al., U.S. Pat. No. 5,902,603)

The stabilizer in the topical formulation 7 includes xanthan gum and xanthan gum equivalents (Fossel, U.S. Pat. No. 9,161,915). The skin penetration enhancer in the topical formulation 7 includes alcohols, amides, amino acids, azone compounds, essential oils, macrocyclic compounds, phospholipids and phosphate compounds, 2-pyrrolidone compounds, sulfoxides, and fatty acid esters. (Hoeck et al., U.S. Pat. No. 6,335,030).

Current products of TD patches on the market are limited by their ability of delivering the drugs at certain rates. For example, the amounts of drug delivered in 24 hours by Butrans (buprenorphine as active ingredient), Neupro (ritigotine as active ingredient), and Exelon (rivastigmine as active ingredient) are delivered at rates of 0.12, 1, and 4.5 mg, respectively. The rate cannot be easily increased because of the nature of the active pharmaceutical ingredients (APIs) and other factors. For example, first of all, a single TD patch can only carry limited amount of the drug delivery medium, as well as the drug. Secondly, there are limited choices for the drug delivering media, which usually consist of adhesive systems (for Matrix type). For some TD-patch types, an added barrier (e.g. a membrane for the Reservoir system) is needed, which further limits the rate of drug delivery. These characteristics imply that a patch is not a suitable drug delivery system for an active pharmaceutical ingredient (API) that requires a higher dose to reach effective level in a human body (i.e. in the range of 10-100 mg/24 hours).

In a preferred form of the present invention, the "applicator-based transdermal drug delivery system" (ABTDS) described herein is potentially capable of delivering drugs at higher rates compared with TD patches for the following reasons: 1) the applicator 6 can handle a much larger or adjustable quantity of the drug delivery medium (i.e. a topical formulation); 2) the choice of the media is not limited to types of adhesive systems because they are no longer an integral part of the delivery system; 3) the specially designed applicator 6 provides additional opportunities in increasing rate of drug delivery by increasing the skin contacting area, as well as reducing the penetration distance for the APIs.

In a further preferred form of the present invention, a topical formulation 7 of ibuprofen is prepared in the form of a cream, a foam, a gel, a lotion, an ointment or other topical formulations 7, which will be used to reduce fever in infants and toddlers, or patients with Alzheimer's disease.

Detailed Description with Respect to the Drawings:

Turning firstly to FIG. 1, there is provided an oval-shaped disk-like applicator 6 which is mounted on a backing layer of a medical tape 4 via an adhesive layer 5. The backing layer prevents passage of the drug or environmental moisture through the surface of the delivery system and provides support for the system. The backing layer is impermeable to the drug or inactive components in the formulation and can be flexible. Suitable materials for the backing layer include polyester, polyethylene terephthalate, some type of nylon, polypropylene, metallized polyester films, polyvinylidene chloride and aluminum foil (Hoeck et al., U.S. Pat. No. 6,335,030). Suitable materials for the adhesive layer 5 include acrylate polymer and polyisobutylene, in which zinc oxide and magnesium oxide and the like are used as cross-linking agents for carboxylic acid groups (Burton et al., U.S. Pat. No. 5,948,433).

The applicator 6 can be made of plastic and/or metallic materials approved for pharmaceutical/medical device applications. Circling edge of the device is a rim 3, of which the height can be varied to optimize effectiveness of the device in containing the topical formulations 7 and in drug delivery. On surface of the device within the circling rim 3, there are blunt spikes 2 that can be in various numbers, sizes and shapes. The applicator 6 may be made of materials of polymers and metal foils with a suitable thickness that will maintain the desired shape while provide certain degree of flexibility. Suitable polymers may include, for example, polyesters, polycarbonates, polyethylenes, polypropylenes, polyvinyl chlorides and polyethylene terephthalate. Suitable metal foils may include, for example, aluminum and stainless steel. The height of the rim 3 is from about 600 to about 3500 micrometers. The ratio between the height of the rim 3 and the height of the blunt spikes 2 are in the range of 0.5 to 1.5 and may be optimized based on the physical characteristics of the formulation and the site of application. When applied, the topical formulation 7 will fill the space on the device between the spikes and within the rim 3.

Figure 2:
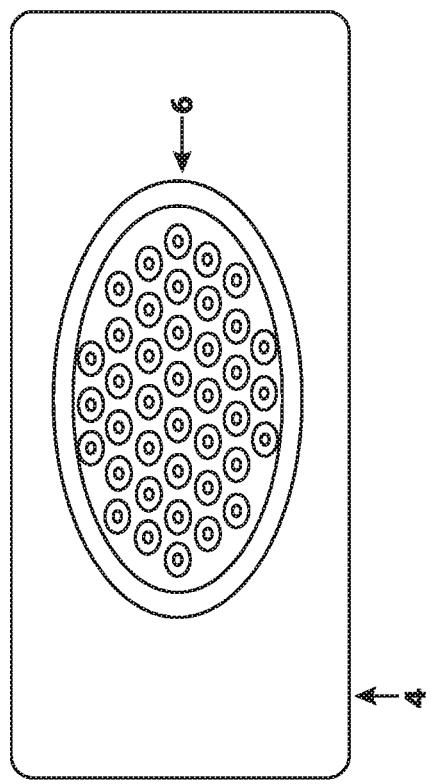
FIG. 2 is an expanded view of a transdermal drug delivery system showing placement of the applicator on a piece of medical tape.

As shown in FIG. 2, a piece of medical tape 4 is used to affix the applicator 6 on the skin of a user.

As used herein, "a" or "an" means one or more (or at least one). For example, a topical formulation 7 comprises a stabilizer and a skin penetration enhancer, which means the topical formulation 7 can contain more than one stabilizer and more than one skin penetration enhancer.

"About" used herein refer to in the range of ±20% of the target point, for example, "from about 600 to about 3500 micrometers" means from the range of 480-720 micrometers to the range of 2800-4200 micrometers.

As used herein, "patient" means either a human or a non-human being such as dog, to which the transdermal drug delivery system is applied.

Although the invention has been explained in relation to its preferred embodiment, it is to be understood that many other possible modifications and variations can be made without departing from the spirit and scope of the invention.

What is claimed is:

1. A transdermal drug delivery system for delivering a drug to a patient comprising an applicator which is mounted on a backing layer of a medical tape via an adhesive layer, and a topical formulation comprising a suitable amount of a drug, wherein the backing layer is impermeable to the drug or inactive components in the topical formulation, wherein the suitable amount of drug penetrates a skin after applying the transdermal drug delivery system to the skin of a patient, wherein the applicator has a rim to define a sealed space and has blunt spikes present on a surface of the applicator and in the sealed space of the rim, wherein the topical formulation is filled in the sealed space of the applicator between the blunt spikes and the rim, wherein the applicator has different shapes and sizes, which can be optimized for delivering the suitable amount of the drug, wherein the total number of the blunt spikes is decided based on an optimized rate of drug delivery, wherein the size and shape of each blunt spike is decided based on the optimized rate of drug delivery, wherein the blunt spikes serve the purpose of holding the topical formulation and increasing the total surface area in contact with the skin when the transdermal drug delivery system is applied to the patient, wherein the topical formulation comprises (1) a suitable concentration of the drug in a pharmaceutically acceptable carrier for delivering a given dose of an active ingredient trans-dermally, (2) a component of a stabilizer and/or a skin penetration enhancer, and (3) various components with an optimized ratio to maintain chemical and physical stability of a drug delivery medium, wherein a height of the rim is larger than a height of each of the blunt spikes, wherein the ratio between the height of the rim and the height of each of the blunt spikes is larger than 1 and is not larger than 1.5, wherein the applicator is made of materials of polycarbonates, wherein the topical formulation comprises the skin penetration enhancer wherein the skin penetration enhancer is azone compounds, wherein the drug in the topical formulation is a nonsteroidal anti-inflammatory drug (NSAID) that is suitable for transdermal delivery, wherein the NASID is naproxen.

2. The transdermal drug delivery system according to claim 1, wherein the applicator has different shape being square, rectangular, circular or oval.

3. The transdermal drug delivery system according to claim 1, wherein the height of the rim is from about 600 to about 3500 micrometers.

4. The transdermal drug delivery system according to claim 1, wherein the topical formulation is prepared in the form of a cream, a foam, a gel, a lotion or an ointment.

5. The transdermal drug delivery system according to claim 1, wherein the topical formulation comprising the component of stabilizer selected from the group consisting of xanthan gum, xanthan gum equivalents and a combination thereof.

6. A method for transdermal delivery of a drug to a patient, the method comprising applying a transdermal drug delivery system to a skin of a patient, wherein the transdermal drug delivery system comprises an applicator which is mounted on a backing layer of a medical tape via an adhesive layer, and a topical formulation comprising a suitable amount of a drug, wherein the backing layer is impermeable, to the drug or inactive components in the topical formulation, wherein the suitable amount of the drug penetrates the skin after applying the transdermal drug delivery system to the skin of the patient, wherein the applicator has a rim to define a sealed space and has blunt spikes present on a surface of the applicator and in the sealed space of the rim, wherein the topical formulation is filled in the sealed space of the applicator between the blunt spikes and the rim, wherein the applicator has different shapes and sizes, which can be optimized for delivering the suitable amount of the drug, wherein the total number of the blunt spikes is decided based on an optimized rate of drug delivery, wherein the size and shape of each blunt spike is decided based on the optimized rate of drug delivery, wherein the blunt spikes serve the purpose of holding the topical formulation and increasing the total surface area in contact with the skin when the transdermal drug delivery system is applied to the patient, wherein the topical formulation comprises (1) a suitable concentration of the drug in a pharmaceutically acceptable carrier for delivering a given dose of an active ingredient trans-dermally, (2) a component of a stabilizer and/or a skin penetration enhancer, and (3) various components with an optimized ratio to maintain chemical and physical stability of a drug delivery medium, wherein a height of the rim is larger than a height of each of the blunt spikes, wherein the ratio between the height of the rim and the height of each of the blunt spikes is larger than 1 and is not larger than 1.5, wherein the applicator is made of materials of polycarbonates, wherein the topical formulation comprises the skin penetration enhancer wherein the skin penetration enhancer is azone compounds, wherein the drugs in the topical formulation is a nonsteroidal anti-inflammatory drug (NSAID) that is suitable for transdermal delivery, wherein the NASID is naproxen.

7. The method according to claim 6, wherein the applicator has different shape being square, rectangular, circular or oval.

8. The method according to claim 6, wherein the height of the rim is from about 600 to about 3500 micrometers.

9. The method according to claim 6, wherein the topical formulation is prepared in the form of a cream, a foam, a gel, a lotion or an ointment.

10. The method according to claim 6, wherein the topical formulation comprising the component of stabilizer selected from the group consisting of xanthan gum, xanthan gum equivalents and a combination thereof.

11. The method for transdermal delivery of drugs according to claim 6, wherein the patient is an infant or a toddler.

12. The method for transdermal delivery of drugs according to claim 6, wherein the patient is a patient with Alzheimer's disease.

13. The method for transdermal delivery of drugs according to claim 6, wherein the patient is a non-human being.

14. The method for transdermal delivery of drugs according to claim 13, wherein the patient is a dog.

* * * * *